United States Patent [19]
Hayes et al.

[11] Patent Number: 5,997,574
[45] Date of Patent: *Dec. 7, 1999

[54] RHEOLOGICALLY MODIFIED AND OSMOTICALLY BALANCED FILL MATERIAL FOR IMPLANT

[75] Inventors: Thomas G. Hayes, Minneapolis; Kenneth C. Kredovski, Roseville; Robert M. Hume, III, Woodbury, all of Minn.

[73] Assignee: Novamed Medical Products Manufacturing, Inc., Minneapolis, Minn.

[ * ] Notice: This patent is subject to a terminal disclaimer.

[21] Appl. No.: 08/924,457

[22] Filed: Aug. 29, 1997

Related U.S. Application Data

[63] Continuation of application No. 08/512,584, Aug. 8, 1995, Pat. No. 5,662,708.

[51] Int. Cl.⁶ .................................................. A61F 2/12
[52] U.S. Cl. .................................... 623/8; 623/7; 623/11; 623/66
[58] Field of Search ........................... 623/7, 8, 11, 66

[56] References Cited

U.S. PATENT DOCUMENTS

| | | |
|---|---|---|
| 4,657,553 | 4/1987 | Taylor . |
| 4,731,081 | 3/1988 | Tiffany et al. . |
| 4,772,284 | 9/1988 | Jefferies et al. . |
| 5,066,303 | 11/1991 | Bark et al. . |
| 5,067,965 | 11/1991 | Ersek et al. . |
| 5,116,371 | 5/1992 | Christensen et al. . |
| 5,273,767 | 12/1993 | Burgum . |
| 5,282,857 | 2/1994 | Perry et al. . |
| 5,407,445 | 4/1995 | Tautvydas et al. . |
| 5,500,017 | 3/1996 | Bretz et al. . |
| 5,658,329 | 8/1997 | Purkait ........................................ 623/8 |
| 5,662,708 | 9/1997 | Hayes et al. ................................ 623/6 |

FOREIGN PATENT DOCUMENTS

| | | |
|---|---|---|
| 0 466 300 | 1/1992 | European Pat. Off. . |
| 462 974 | 9/1990 | Sweden . |
| 9320780 | 10/1993 | WIPO . |

OTHER PUBLICATIONS

Excerpt from U.S. Patent 4,780,543 which sets forth the molecular weight range of agar Oct. 1988.

*Primary Examiner*—Paul B. Prebilic

[57] ABSTRACT

A rheologically modified, osmotically balanced dispersion for an implant for the body. The dispersion includes an osmotic control agent of preferably polyvinylpyrrolidinone, a rheological agent of preferably guar gum, and an antimicrobial. Methods for filling an implant are also disclosed. The osmotic control agent or first polymeric agent is present in the dispersion in an amount effective to substantially balance the osmotic pressure of the implant with the osmotic pressure of the portion of the body into which it is implanted. The rheological agent or second polymeric agent forms a three-dimensional network and is present in the dispersion in an amount effective such that the fill material is pseudoplastic. Both the first and second polymeric agents are biocompatible.

12 Claims, 1 Drawing Sheet

RHEOLOGICALLY MODIFIED AND OSMOTICALLY BALANCED FILL MATERIAL FOR IMPLANT

This application is a continuation of U.S. patent application Ser. No. 08/512,584 filed Aug. 8, 1995, now U.S. Pat. No. 5,662,708.

BACKGROUND OF THE INVENTION

The present invention relates generally to implants introduced into the body, particularly to fill material for such implants, and specifically to rheologically modified fill material for implants.

For implants such as breast and testes prosthesis as well as other implants and prosthesis, silicone has been the fill material of choice. However, silicone as a fill material has fallen into disfavor. This has prompted efforts to find replacements for silicone. These replacements are often if not always undesirable because such replacements have been unable to match the feel provided by silicone. The inventors of the present invention have investigated the rheological parameters of certain fluid formulations in an effort to provide a fill material having the heretofore unmatched feel of silicone. Thus, it is important to understand some basics of rheology to have an understanding of the present invention.

Rheology is the science of the deformation and flow of matter. It is concerned with the response of materials to mechanical force. Polymer rheology deals with polymeric materials and biorheology deals with biological fluids.

Deformation is the relative displacement of points of a body and can be divided into two general types: flow and elasticity. Flow is irreversible deformation; when the stress is removed, the material does not revert to its original configuration. Elasticity is reversible deformation; the deformed body recovers its original shape.

The usual way of defining the rheological properties of a material is to determine the resistance to deformation. Resistance to deformation is measured by two indexes or yardsticks: 1) viscosity (the index or yardstick for flow; viscosity is the resistance to flow of a liquid); and 2) the degree of elasticity (elastic deformation).

A liquid is a material that continues to deform as long as it is subjected to a tensile or shear stress. For a liquid under shear, the rate of deformation (shear rate) is proportional to the shearing stress.

Thixotropy is the decrease in viscosity with time when sheared at a constant shear rate. Rheopexy, a relatively rare occurrence; is the increase in viscosity of a fluid in response to shear. For example, as to thixotropy, when a shearing action begins, such as when one applies a latex house paint with a brush, the viscosity decreases quickly to permit the paint to be easily brushed to a thin film and provide a short period of time for the brushmarks to level. When the shearing action stops, such as when the paint leaves the brush and clings to the wall, the viscosity of the latex house paint increases to prevent running and sagging. Thixotropy may be a time dependent effect.

A single fluid may be subject to a number of shear rates. For example, a paint may be pumped during manufacture or immediately prior to application (intermediate shear rate),, sprayed onto a wall (high shear rate), coalesce and flow to form a uniform film (intermediate to low shear rate), and sag or run under gravity (low shear rate). A given liquid or material may work well at one or two of the shear rates, but fail at other shear rates.

SUMMARY OF THE INVENTION

General objects of the present invention include a unique rheologically modified dispersion for an implant for a body and unique methods for filling the implant.

Another object of the present invention is to provide such a rheologically modified dispersion which uniquely includes an osmotic control agent.

Another object of the present invention is to provide such a rheologically modified dispersion wherein the osmotic control agent uniquely includes a poly-N-vinylamide.

Another object of the present invention is to provide such a rheologically modified dispersion wherein the poly-N-vinylamide uniquely includes polyvinylpyrrolidinone.

Another object of the present invention is to provide such an osmotically controlled and rheologically modified dispersion wherein the rheological agent uniquely includes a three-dimensional network.

Another object of the present invention is to provide such an osmotically controlled and rheologically modified dispersion wherein the three-dimensional rheological agent uniquely includes gum.

Another object of the present invention is to provide such an osmotically controlled and rheologically modified dispersion wherein the gum uniquely includes a natural gum.

Another object of the present invention is to provide such an osmotically controlled and rheologically modified dispersion wherein the natural gum uniquely includes guar gum or locust bean gum and their derivatives.

Another object of the present invention is to provide such an osmotically controlled and rheologically modified dispersion wherein the gum uniquely includes xanthan and its derivatives.

Another object of the present invention is to provide such an osmotically controlled and rheologically modified dispersion wherein the gum uniquely includes a synthetic gum.

Another object of the present invention is to provide such an osmotically controlled and rheologically modified dispersion wherein the synthetic gum uniquely includes poly (vinyl alcohol), polyethylene oxide, polypropylene oxide, polyacrylamide, or copolymers of polyvinylpyrrolidinone.

Another object of the present invention is to provide such an osmotically controlled and rheologically modified dispersion which uniquely is a pseudoplastic. Such a pseudoplastic dispersion mimics the rheology of body fluid and tissue.

Another object of the present invention is to provide such an osmotically controlled and rheologically modified dispersion in which uniquely all of the components of the dispersion are biocompatible. Accordingly, even in the worst case scenario in which the implant bursts, little or minimal danger is presented.

An advantage of the present invention is that the fill material of an implant is osmotically balanced with its environment. With an osmotic balance, the implant retains its desired volume. Such is in contrast to an implant which includes a low osmotic pressure; here, water or another solvent flows out of the implant, perhaps causing fold flaw fracture. A high osmotic pressure in the implant may lead to a bursting of the implant.

Another advantage of the present invention is that the fill material is rheologically modified to be pseudoplastic. This provides a feel or responsive fill material which mimics body tissue.

These and further objects and advantages of the present invention will become clearer in light of the following

Figure 1:
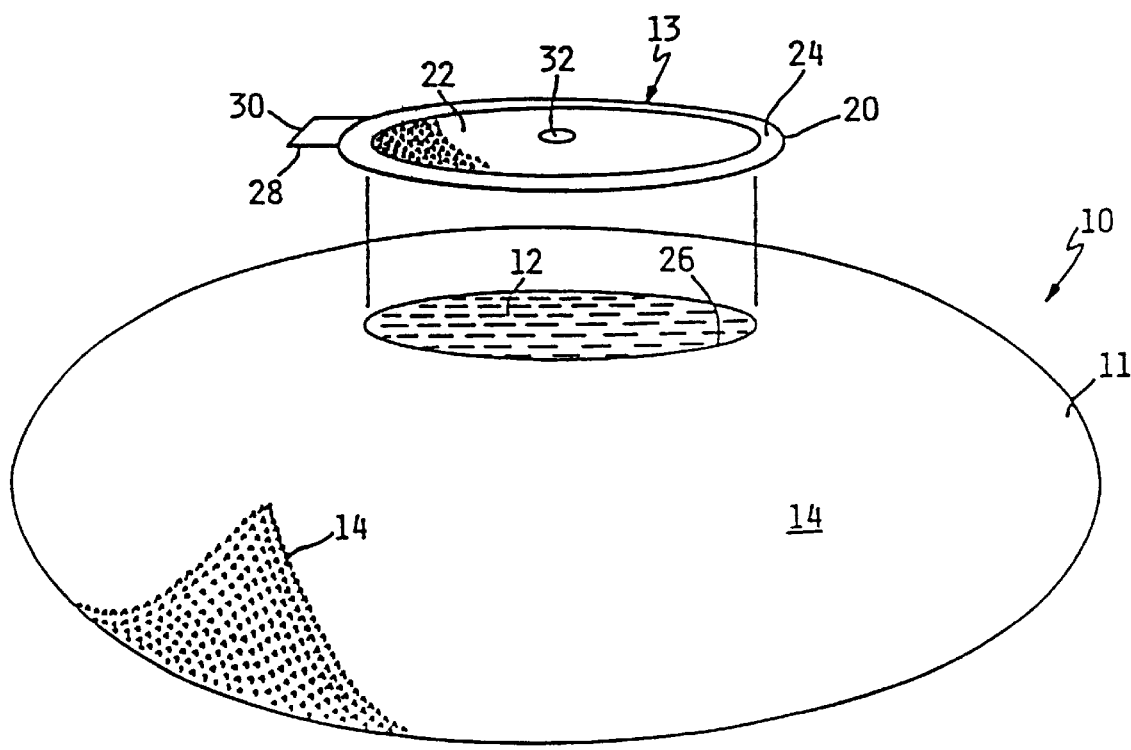
FIG. 1 shows a perspective, partially exploded view of a breast implant.

All Figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "inner", "outer", and "upper" and similar terms are used herein, it should be understood that these terms have reference only to the structure shown in the drawings as it would appear to a person viewing the drawings and are utilized only to facilitate describing the preferred embodiments.

DESCRIPTION

In general, the present invention relates to a safe fill material for an implant. The fill material preferably includes water, an osmotic control agent such as a poly-N-vinylamide or polyvinylimide, a rheological agent such as a gum. Optionally, the fill material may include cross-linkers for the rheological agent (i.e. the thixotrope or gellant) and/or other additives such as antioxidants, preservatives such as antimicrobials, wetting agents, and lubricants. The fill material is biocompatible.

Osmotic control agent, for the purposes of the present invention, means that which is added to the fill material to prevent or minimize osmosis, i.e. flow of solvent (water) through the membrane of the implant. Osmosis is minimized by providing the interior of the implant with an osmotic pressure which is equal to the osmotic pressure of the environment outside of the implant. Accordingly, osmotic control agent further means that which provides an osmotic pressure similar to the body or body tissue or fluid or to the portion of the body into which the implant is to be located. The most preferred osmotic pressure provided by the osmotic control agent, when combined with the rheological agent of the present invention, is between about 250 and about 350 milliosmoles.

Still further, the osmotic control agent is a polymer or polymers or copolymer or copolymers that contributes substantially to the desired osmotic pressure of between about 250 and 350 milliosmoles. Such a substantial contribution is made when the polymeric osmotic control agent is added to the fill material preferably in an amount between about 90% to 99.9% w/w, more preferably between about 95% to 99.9% w/w, and most preferably between about 98% to 99% w/w of the osmotic control agents. If required, salts may be added to fine tune the osmotic pressure of the implant. These salts preferably include biocompatible salts such as sodium chloride, sodium lactate and sodium acetate in an amount of between about 1% and 10% w/w of the osmotic control agents. For radiolucency, sodium lactate and sodium acetate are preferred. It should be noted that osmotic pressure is a colligative property that depends on the number of solute particles.

Still further, it should be noted that osmotic control agents which are preferred provide lubricity to the interior wall of the implant. In sum, it is preferred that the osmotic control agent: 1) is a polymer or copolymer or blend thereof; 2) is present in an amount effective to provide an osmotic pressure to the implant of between about 250 and 350 milliosmoles without the use of salts; and 3) is present in an amount effective to provide lubricity to the fill material (i.e. to the interior wall of the implant).

The osmotic control agent is preferably a protective colloid which is water-soluble or water-dispersable. Examples of preferred colloids include poly-N-vinylamides, poly-N-vinylamide copolymers, polyvinylimides. Poly-N-vinylamide hydrogels are most preferred.

The poly-N-vinylamides may be either linear or cyclic. Examples of poly-N-vinylamides prepared from linear derivatives include poly(acetamide), poly(methylacetamide), poly(ethylacetamide), poly(phenylacetamide), poly(methylpropionamide), poly(ethylpropionamide), poly(methylisobutyramide), and poly(methylbenzylamide). Poly-N-vinylamides derived from cyclic structures are more preferred. Examples of these polymers include polyvinylpyrrolidinone, polyvinylcaprolactam, poly-2-piperidinone, poly-5-methyl-2-pyrrolidinone, poly-2,2,5-trimethyl-2-pyrrolidinone, and poly-5-methyl-2-pyrrolidinone. Polyvinylpyrrolidinone and polyvinylcaprolactam are even more preferred with polyvinylpyrrolidinone being most preferred.

Polyvinylpyrrolidinone (PVP or povidone or poly(N-vinyl-2-pyrrolidinone)) is one of the few poly-N-vinylamides prepared from cyclic structures, if not the only one, available in a commercial quantity. Polyvinylcaprolactam has been commercialized to some extent.

Poly-N-vinylamide copolymers include poly(vinylpyrrolidinone-co-vinyl acetate), poly(vinylpyrrolidinone-co-maleic anhydride), poly(vinylpyrrolidinone-co-methyl methacrylate), poly(vinylpyrrolidinone-co-dimethylaminoethyl methacrylate), poly(vinylpyrrolidinone-co-butyl methacrylate), poly(vinylpyrrolidinone-co-hydroxyethyl methacrylate), poly(vinylpyrrolidinone-co-ethyl acrylate), poly(vinylpyrrolidinone-co-ethylhexyl acrylate), poly(vinylpyrrolidinone-co-acrylic acid), poly(vinylpyrrolidinone-co-acrylamide), poly(vinylpyrrolidinone-co-acrylonitrile), polyvinylpyrrolidinone-co-styrene), poly(vinylpyrrolidinone-co-ethylene), and poly(vinylpyrrolidinone-co-crotonic acid) and their derivatives.

For the purposes of the present invention, the molecular weight of the osmotic control agent is in the range of preferably about 1000 to about 100,000, more preferably about 1000 to about 40,000, and even more preferably about 3000 to about 20,000, and most preferably about 10,000. Poly-N-vinylamides, such as PVP, at molecular weights higher than about 100,000 may not be excretible from the human body. Poly-N-vinylamides, such as PVP, at weights below about 100,000 may be bioexcretable, with those having molecular weights below 30,000 being more likely to be quickly excretable, such as through the human kidney. The molecular weights noted herein are in daltons.

A higher molecular weight of the poly-N-vinylamide, such as PVP, generally relates to a higher degree of polymerization and a greater intrinsic viscosity. Further, the viscosity of the poly-N-vinylamide (such as PVP) in water generally increases with the solid concentration.

In the fill material according to the present invention, the osmotic control agent is present in the range of preferably from about 0.5% to about 60%, more preferably from about 2.5% to about 40%, and most preferably from about 3.5% to about 20%(w/w).

Such a range of concentration, when combined with one or more of the rheological agents of the present invention, provides an osmolarity of preferably between about 100 milliosmoles and about 500 milliosmoles, more preferably between about 200 milliosmoles and about 400 milliosmoles, and most preferably between about 250 and about 350 milliosmoles. It should be noted that such an osmolarity is preferably obtained without the use of salts. It should further be noted that PVP, when alone in solution without a three dimensional network, does not provide the desired pseudoplasticity to the solution.

Rheological agent means a material which modifies the normal solution properties to increase or decrease its resistance to flow and to increase or decrease its elasticity. Rheological agent further means that which provides a pseudoplasticity to the fill material to the implant. The fill material of the present invention as a whole is pseudoplastic. In other words, when shear stress is applied to the fill material, the viscosity of the fill material is reduced in proportion to the amount of shear. Upon release of the shear, total viscosity recovery of the fill material occurs almost instantaneously.

That the fill material of the present invention is pseudoplastic is advantageous. This feature of decreased apparent viscosity at high shear rates facilitates mixing, pumping, and pouring. Further, when in the body, such pseudoplasticity mimics body tissue and fluid, such as the breast body tissue and fluid. For example, the undesired bounce of conventional saline implants is minimized.

The rheological agent includes pseudoplastic agents or thixotropic agents. Pseudoplastic agents are preferred.

The rheological agent is preferably a polymer which provides a three-dimensional network within the implant. This three-dimensional network provides a backbone for the polymeric osmotic control agent, which may contribute in part to the three-dimensional network.

The rheological agent is preferably one which contributes little to the osmotic pressure of the implant. As noted above, osmotic pressure is a colligative property that depends on the number of solute particles. With the present invention, even though it is a massive "particle", the polymeric rheological agent and its three-dimensional network behaves like a single particle. Accordingly, it contributes little to the osmotic balance. Conversely, a portion of the polymeric osmotic control agent contributes to the three-dimensional network, while the remaining portion of the polymeric osmotic control agent dictates the osmotic pressure of the fill material in the implant. It is believed that the combinations of the present invention are synergistic; that is, the osmotic pressure of the present invention relates little, if at all, to a corresponding amount of an osmotic control agent dispersed only in water.

Advantageously, it should be noted that the polymeric osmotic control agents of the present invention move through the three-dimensional network relatively slowly. In contrast, salts are distributed rather quickly even in the presence of a three-dimensional network of the present invention.

The rheological agent is preferably a gum which is water-dispersible. Examples include gums which are natural polymers and gums which are synthetic polymers. Examples of natural polymer gums include polysaccharides, proteins, and natural rubbers and chemically modified natural polymers such as hydroxyethylcellulose. Examples of synthetic polymer gums include polyvinyl alcohol) and polyethylene oxide. Generally, the rheological agent is added to the fill material in a concentration of preferably from about 0.05% to about 36%, more preferably from about 0.1% to about 24%, even more preferably from about 0.1% to about 12%, and most preferably from about 0.1% to about 2.0% (w/w).

A gum is a polymeric substance which, in an appropriate solvent or swelling agent, form highly viscous dispersions or gels at low, dry substance content. Gums may or may not be water-soluble.

The gum preferably is a water soluble polysaccharide (glycan). Examples include seed gums such as corn starch, guar gum, and locust bean gum; tuber and root gums such as potato starch and tapioca starch; seaweed extracts such as algin, carageenan, agar, and furcellaran; plant extracts such as pectin; exudate gums such as gum arabic; fermentation (microbial) gums such as xanthan (qv), dextran (qv) and welan (polysaccharide S-130); and derived gums such as carboxymethylcellulose, hydroxyalkylmethylcellulose, methylcellulose, starch acetate, starch phosphate, hydroxyethylstarch, hydroxypropylstarch, oxidized starches, and dextrinized starches. Seed gums are most preferred. Of the seed gums, guar gum is most preferred. The glycan is added to the fill material in a concentration of preferably from about 0.1% to about 25%, more preferably from about 0.1% to about 15%, and most preferably from about 0.01% to about 10% (w/w).

Examples of gums which are galactommannans (a polymer of D-galactose and D-mannose) include guaran (the purified polysaccharide from guar gum), locust bean gum, and tara gum. Of these guaran is preferred. Guar gum, locust bean, and tara gum also means, for the purposes of the present invention, their blends, and the endosperms, high purity splits, derivatives, granules, and powders of such gums. Examples of guar derivatives include hydroxypropyl-, hydroxyethyl-, sodium carboxymethyl-, sodium carboxymethylhydroxypropyl-, and 2-hydroxypropyl(trimethyl) ammonium guar gums.

The galactommannan is added to the fill material in a concentration of preferably from about 0.05% to about 6%, more preferably from about 0.1% to about 4.0%, and most preferably from about 0.1% to about 2% (w/w).

Chemically modified natural polymers or derived gums preferably include cellulose derivatives such as an hydroxyalkylcellulose. Examples of hydroxyalkylcellulose include carboxymethylcellulose, hydroxyethylcellulose, hydroxypropylcellulose, ethylhydroxyethylcellulose. The derived gum is added to the fill material in a concentration of preferably from about 0.5% to about 30%, more preferably from about 5% to about 25%, and most preferably from about 8% to about 15% (w/w).

Xanthan (or xanthan gum) may be used as the sole rheological agent of the present invention or in combination with locust bean and/or guar gum. When used alone, xanthan is added to the fill material in a concentration of preferably from about 0.05% to about 6%, more preferably from about 0.1% to about 4.0%, and most preferably from about 0.1% to about 2.0% (w/w).

The amount of xanthan in locust bean gum or in a locust bean/guar gum blend may be between about 1% and about 99% w/w. The amount of locust bean or guar gum in such a blend may be between about 1% and about 99% w/w. The xanthan and/or locust bean and/or guar blend is added to the fill material in a concentration preferably from about 0.05% to about 6%, more preferably from about 0.1% to about 4.0%, and most preferably from about 0.1 to about 2% (w/w).

Examples of synthetic polymer gums, where such form biocompatible water-dispersable and water-soluble gums, include poly(vinyl alcohol), polyethers such as the poloxamers polyethylene oxide and polypropylene oxide, polyacrylamide, their copolymers and blends, and copolymers of poly-N-vinylamides, including copolymers of polyvinylpyrrolidinone such as poly(N-1-vinylpyrrolidone)-co-2-methylaminoethylmethacrylate, poly(1-vinylpyrrolidone)-co-acrylic acid, and poly(1-vinylpyrrolidone)-co-vinylacetate. As to polyethylene oxide and polypropylene oxide and their copolymers and blends, the totality of the Tautvydas et al. U.S. Pat. No. 5,407,445 is hereby incorporated by reference.

The synthetic polymer gum is added to the fill material in a concentration of preferably from about 0.5% to about 60%, more preferably from about 0.5% to about 40%, and still more preferably from about 0.5% to about 20%(w/w). Still further, in the case of polyethylene oxide or polypropylene oxide, the most preferred range is about 0.6% to about 5.0% of the fill material. Of the biodegradable synthetic polymers, poly(vinyl alcohol) and polyethylene oxide are preferred.

The gum of the present invention preferably includes those gums which have been identified as the safest gums for an implant in the body. Such gums include guar, a cellulose derivative (selected from the group of carboxymethylcellulose, hydroxyethylcellulose, hydroxypropylcellulose, ethylhydroxyethylcellulose), xanthan, a xanthan/locust bean mixture, polyethylene oxide, and poly(vinyl alcohol). Guar, polyethylene oxide, and poly(vinyl alcohol) are most preferred.

It should be noted that it is preferred that the rheological agent of the present invention is one which contributes little, if any, to the osmotic pressure of the implant fill material. As osmolarity is a function of the number of particles, it is preferred that the rheological agent have a sufficiently high molecular weight. Guar, for example, typically includes a molecular weight between about 200,000 and about 240,000. Locust bean gum typically includes a molecular weight between about 300,000 and 360,000. The compound (or compounds) forming the three-dimensional network includes a molecular weight preferably between about 4000 and 4,000,000, and more preferably between about 100,000 and 600,000.

An example of a biocompatible compound which forms a three-dimensional network but which is neither a gum nor a polymer is gelatin. Gelatin is a heterogeneous mixture of water-soluble proteins of high average molecular weight. Gelatin is not found in nature but is derived from collagen. Gelatin may be obtained by boiling skin, tendons, ligaments, bones, etc. with water.

Examples of means for preventing microbial growth include irradiation (gamma radiation) of the fill material and antimicrobial preservatives such as benzoates and parabens, and non food grade preservatives. The preservatives are added to the fill material in concentrations at or less than about 1% w/w, or more preferably at or less than about 0.5% w/w, and still more preferably at or less than 0.25% w/w.

It should be noted that the rheological agents of the present invention include those rheological agents which have been irradiated prior to introduction into the dispersion or formation of gum. These pre-irradiated rheological agents include pre-irradiated guar or xanthan gums. As to pre-irradiated rheological agents, the totality of the Burgum U.S. Pat. No. 5,273,767 is hereby incorporated by reference.

Optionally, the fill material includes a reactant such as a cross-linking agent for the rheological agent. These cross-linking agents include $Al_2(SO_4)_3$ and its analogs, borates such as borax, boric acid and its analogs, titonates, chrome complexes, zirconium, and calcium compounds. Generally, these cross-linking agents are added to the fill material in a concentration of preferably at or less than 1% w/w and more preferably at or less than 1% of the concentration of the rheological agent. Cross-linking or hydrogen bonding in the three-dimensional network of the present fill material may provide a viscoelastic fill material.

It should be noted that one object of the present invention is to provide a safer fill material for an implant. A safer fill material is one which includes the least possible amount of nontoxic foreign components.

It should be noted that the lubricity of the fill material is preferably provided by the polymeric osmotic control agent, such as the colloid, the poly-N-vinylamide, or polyvinylpyrrolidinone. The amount of the polymeric osmotic control agent effective to provide an osmotic pressure to the implant of between about 250 and 350 milliosmoles is more than required to provide lubricity to the fill material.

The viscosity, or apparent viscosity, of the fill material is in the range of preferably between about 100 and 20,000 centipoise, more preferably between about 200 and about 10,000 centipoise, and most preferably between about 400 and about 5000 centipoise.

The implant according to the present invention may be a breast or testes prosthesis, a penile-implant, or an implant containing a drug to be dispersed over time. The shell of the implant may be permeable or impermeable. For example, the shell may be permeable to water vapor or may be impermeable to water vapor, or may be permeable to other fluids or compounds such as drugs or pharmaceutical agents. Examples of shells which are permeable to water vapor include the shell set forth in U.S. patent application Ser. No. 08/473,284, filed Jun. 7, 1995, the totality of which is hereby incorporated by reference. Examples of shells which are permeable to water vapor include the conventional silicone or polyurethane shell.

A breast implant is shown in FIG. 1. It includes a shell 11, a fill material 12 of the present invention, and a closure or joint 13 for closing the shell 11 and sealing the fill material therein. The closure 13 is a room temperature vulcanized silicone button seal. The closure 13 is formed of the same material as the shell 11 and includes an inner disk shaped silicone layer 20 having a greater diameter than the outer disk shaped layer 22 such that an annular portion 24 of the inner layer 20 extends beyond the outer layer 22. The outer surface of the annular portion 24 is bonded via a vulcanized weld to the inner surface of the shell 11. The outer disk shaped layer 22 has a diameter substantially equal to the diameter of the opening 26 formed by the mandrel in the manufacture of the shell 11. A leaf valve assembly or primary closure 28 is fixed to the inner surface of the disk shaped portion 20. The leaf valve assembly 28 includes an outlet 30 and an inlet disposed adjacent to the center of the disk shaped portion 20. The opposing flap sides of the leaf valve assembly 28 cling together to minimize passage of fluid through the assembly 28. After the closure 13 has been vulcanized to the shell 11 to close the shell 11, a needle filled with the filling material 12 penetrates the closure 13 and extends into the inlet of the leaf assembly 28. The needle is then operated to push the fill material 12 into the shell 11. After the shell has been filled, a pocket of air typically exists in the upper portion of the shell 11. This air may be withdrawn by operation of the needle. The hole formed in the center of the closure 13 by the penetration of the needle is then sealed with a biocompatible silicone to form the domed button seal or secondary closure 32. It should be noted that the closure 13 may alternatively include a valve such as compression valve or septa. As noted above, the shell 11 may be of a material which is permeable or impermeable to water vapor. The shell 11 may be silicone, polyurethane, or another elastomeric material.

Figure 2:
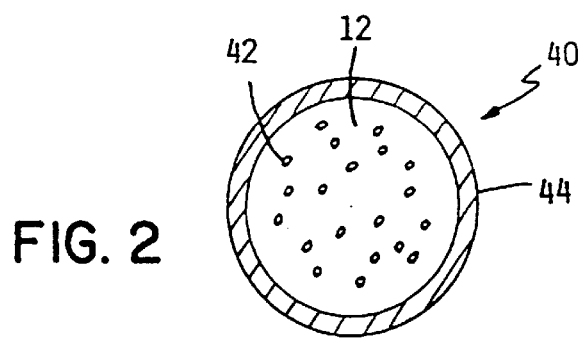
FIG. 2 shows a section view of an implant with a dispersion containing a drug to be released over time.

FIG. 2 shows an implant 40 containing the fill material 12 and a drug or pharmaceutical or therapeutic agent 42 to be dispersed over time. The implant 40 includes a spherical ovoid or coin-like shell 44 which is permeable or semipermeable relative to the agent 42. When the shell is silicone, examples of the agent include silicone permeable hormones such as progesterone, Estradiol including 17-B-Estradiol, Melatonin, and Levonorgestrel, silicone permeable narcotic analgesics such as Fentanyl and morphine sulfate, and silicone permeable antianginal agents or vasodilators such as nitroglycerin.

Procedures for filling the implants include the following method. The temperature of double distilled water is adjusted to 35° F. (1.67° C.). The components are then preferably added to the double distilled water in the following order: the preservative if desired, the cross-linking agent if desired, the osmotic control agent, and then the rheological agent. Then the dispersion is agitated and the temperature of the dispersion is permitted to rise in an environment at room temperature until the desired swelling has occurred. The dispersion is then injected into the implant. The implant is then rotated such that the dispersion remains uniformly dispersed, thereby allowing the rheological agent to fully hydrate (and cross-link if a cross-linking agent has been added to provide a three dimensional network if the rheological agent alone does not provide such).

It should be noted that "biocompatible" means that which remains in unchanged form in the body without causing adverse reaction, that which may be metabolized, and/or that which may be excreted without being metabolized.

It should further be noted that the fill material of the present invention is radiolucent. The fill material is not radiographically dense, nor does the fill material result in under-exposure of x-ray film. The fill material includes an optical density from about 1.2 to about 1.3 and an x-ray penetrance of from about 9.2 to about 30 milliroentgens. The osmotic control agents and rheological agents of the present invention include elements with relatively low atomic numbers which do not interfere with radiolucency.

EXAMPLE 1

(PVP and Guar)

Eight hundred (800) grams of high purity water were mixed with 200 g of PVP [poly(2-vinylpyrrolidone), Povidone K-17, (ISP Povidone C-15)] at room temperature to form a yellow liquid. Two and one half grams of methyl-4-hydroxybenzoate and two and one half grams of propyl-4-hydroxybenzoate were added to the PVP solution with vigorous stirring. Fifteen grams of Jaguar 8600 guar gum (Rhone-Poulenc, Specialty Chemical Division, Prospect Plains Road, Cranberry N.J.) were added by carefully dispersing the gum into the vortex of a rapidly (ca 2000 rpm) stirring laboratory mixer to form a responsive gel.

EXAMPLE 2

(PVP and Guar)

Eight hundred (800) grams of high purity water were mixed with 200 g of PVP (poly(2-vinylpyrrolidone)), at room temperature to form a yellow liquid. Two and one half grams of methyl-4-hydroxybenzoate and two and one half grams of propyl-4-hydroxybenzoate were added to the PVP solution with vigorous stirring. Thirty grams of Jaguar 8600 guar gum were added by carefully dispersing the gum into the vortex of a rapidly (ca 2000 rpm) stirring laboratory mixer to form a responsive gel.

EXAMPLE 3

(PVP and Guar)

Eight hundred (800) grams of high purity water were mixed with 200 g of PVP (poly(2-vinylpyrrolidone)) at room temperature to form a yellow liquid. Two and one half grams of methyl-4-hydroxybenzoate and two and one half grams of propyl-4-hydroxybenzoate were added to the PVP solution with vigorous stirring. Forty-five grams of Jaguar 8600 guar gum were added by carefully dispersing the gum into the vortex of a rapidly (ca 2000 rpm) stirring laboratory mixer to form a responsive gel.

EXAMPLE 4

(PVP and Guar)

Eight hundred (800) grams of high purity water were mixed with 200 g of PVP (poly(2-vinylpyrrolidone)) at room temperature to form a yellow liquid. Two and one half grams of methyl-4-hydroxybenzoate and two and one half grams of propyl-4-hydroxybenzoate were added to the PVP solution with vigorous stirring. Fifty-five grams of Jaguar 8600 guar gum were added by carefully dispersing the gum into the vortex of a rapidly (ca 2000 rpm) stirring laboratory mixer to form a responsive gel.

EXAMPLE 5

(PVP and Pectin)

Two hundred grams of a 20% w/w solution of PVP (poly(2-vinylpyrrolidone)) (with a base of high purity water) were mixed with Carex F/G Arabinose Galactan (a pectin from the larch tree) by adding the Galactan to the vortex of rapidly stirred water. The temperature was raised slowly, over the course of one hour, to 97° C. with moderate stirring to form a responsive gel.

EXAMPLE 6

(PVP and Gelatin)

Gelatin (Knox household gelatin) was added to a 20% (w/w) PVP (poly(2-vinylpyrrolidone)) solution as described in Example 1. The dispersion was heated until all the gelatin dissolved forming a clear solution. Upon cooling a responsive gel formed. Several concentrations were prepared using this same technique to provide gels of varying consistency.

EXAMPLE 7

(PVP and Polyethylene Oxide)

Four hundred grams of deionized water and one hundred grams of PVP (poly(2-vinylpyrrolidone)) were mixed with vigorous stirring. To this solution three grams of Polyox 303 (polyethylene oxide, Union Carbide) were added. The rapid formation of a responsive gel was noted.

EXAMPLE 8

(PVP and Polyethylene Oxide)

Four hundred grams of deionized water and one hundred grams of PVP (poly(2-vinylpyrrolidone)) were mixed with vigorous stirring. To this solution three grams of Polyox 303 (polyethylene oxide, Union Carbide) were added. The rapid formation of a responsive gel was noted.

EXAMPLE 9

(PVP and Polyethylene Oxide)

Four hundred grams of deionized water and one hundred grams of PVP (poly(2-vinylpyrrolidone)) were mixed with vigorous stirring. To this solution six grams of Polyox 303 (polyethylene oxide, Union Carbide) were added. The rapid formation of a responsive gel was noted.

EXAMPLE 10

(PVP and Polyethylene Oxide)

Eight hundred grams of deionized water and one hundred grams of PVP (poly(2-vinylpyrrolidone)) were mixed with vigorous stirring. To this solution twenty-five grams of Polyox 303 (polyethylene oxide, Union Carbide) were added. The rapid formation of a responsive gel was noted.

EXAMPLE 11

(PVP and PVP Copolymer)

Two hundred grams of a 20% solution of poly(N-1-vinylpyrrolidone)-co-2-methylaminoethylmethacrylate were mixed with two hundred and fifty-eight grams of high purity water to form a responsive gel. Thirty six grams of PVP (poly(2-vinylpyrrolidone)) were added to the mixture. Upon standing a responsive viscous gel was formed.

EXAMPLE 12

(PVP and PVP Copolymer)

Nine hundred forty-nine grams of 20% (w/w) PVP (poly(2-vinylpyrrolidone)) solution were mixed with fifty-one grams of poly(l-vinylpyrrolidone)-co-acrylic acid were mixed together and heated at 70° C. for one hour to form a responsive gel.

EXAMPLE 13

(PVP and PVP Copolymer)

One hundred grams of poly(1-vinylpyrrolidone)-covinylacetate were mixed with eight hundred and thirty grams of deionized water and mixed with vigorous stirring. Seventy grams of PVP (poly(2-vinylpyrrolidone)) were added to the mixture with vigorous stirring to form a responsive gel.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

It is claimed:

1. A safe, rheologically modified, osmotically balanced, biocompatible, lubricating, water based, implant fill material for an implant for the body, the implant having an inner face, the implant fill material comprising an aqueous dispersion which comprises, in combination:
   a) a rheological control agent which:
      i) is polymeric;
      ii) forms a three-dimensional network in the dispersion;
      iii) is present in the dispersion in an amount effective such that the fill material forms a responsive gel; and
      iv) contributes minimally to osmolarity of the dispersion; and
   b) an osmotic control agent which:
      i) is a polymer or copolymer or blend thereof selected from the group consisting of poly-N-vinylamides, poly-N-vinylamide copolymers, and polyvinylimides;
      ii) is present in the dispersion in an amount effective to substantially balance an osmotic pressure of the implant with the osmotic pressure of the portion of the body into which it is implanted and such that the dispersion has an osmolarity of between about 250 and about 350 milliosmoles;
      iii) functions as a lubricant for the inner face of the implant and is present in an excessive amount for said function as a lubricant; and
      iv) is movable through the three-dimensional network.

2. The implant fill material according to claim 1 wherein the rheological control agent is a gum.

3. The implant fill material according to claim 1 wherein the aqueous dispersion further comprises a cross-linking agent for the rheological control agent.

4. The implant fill material according to claim 1 wherein the osmotic control agent is a hydrogel.

5. The implant fill material according to claim 1 wherein the osmotic control agent is a protective colloid.

6. The implant fill material according to claim 1 wherein the osmotic control agent is polyvinylpyrrolidinone.

7. The implant fill material according to claim 1 wherein the osmotic control agent has a molecular weight from about 3000 to about 20,000 daltons such that bioexcretability of the osmotic control agent is maximized.

8. The implant fill material according to claim 1 wherein the fill material is irradiated to minimize microbial growth.

9. The implant fill material according to claim 1 wherein the fill material is radiolucent.

10. A safe, rheologically modified, osmotically balanced, biocompatible, lubricating, water based, implant fill material for an implant for the body, the implant having an inner face, the implant fill material comprising an aqueous dispersion which comprises, in combination:
    a) a rheological control agent which:
       i) is a gum;
       ii) forms a three-dimensional network in the dispersion;
       iii) is present in the dispersion in an amount effective such that the fill material forms a responsive gel; and
       iv) contributes minimally to osmolarity of the dispersion; and
    b) an osmotic control agent which:
       i) is a polymer or copolymer or blend thereof selected from the group consisting of poll-N-vinylamides poly-N-vinylamide copolymers, and polyvinylimides;
       ii) is a protective colloid;
       iii) is present in the dispersion in an amount effective to substantially balance an osmotic pressure of the implant with the osmotic pressure of the portion of the body into which it is implanted and such that the dispersion has an osmolarity of between about 250 and about 350 milliosmoles;

iv) is a lubricant for the inner face of the implant; and v) is movable through the three-dimensional network.

11. A safe, rheologically modified, osmotically balanced, biocompatible, lubricating, water based, implant fill material for an implant for the body, the implant having an inner face, the implant fill material comprising an aqueous dispersion which comprises, in combination:

a) a rheological control agent which:
  i) is a gum;
  ii) forms a three-dimensional network in the dispersion;
  iii) is present in the dispersion in an amount effective such that the fill material forms a responsive gel; and
  iv) contributes minimally to osmolarity of the dispersion; and b) an osmotic control agent which:
  i) is selected from the group consisting of poly-N-vinylamides, poly-N-vinylamide copolymers, and polyvinylimides;
  ii) is present in the dispersion in an amount effective to substantially balance an osmotic pressure of the implant with the osmotic pressure of the portion of the body into which it is implanted and such that the dispersion has an osmolarity of between about 250 and about 350 milliosmoles;
  iii) is a lubricant for the inner face of the implant; and
  iv) is movable through the three-dimensional network.

12. The implant fill material according to claim 11 wherein the osmotic control agent is poly pyrrolidinone.

* * * * *